United States Patent [19]

Goldenberg

[11] Patent Number: 5,261,872
[45] Date of Patent: Nov. 16, 1993

[54] INGROWN TOENAIL CORRECTION APPLIANCE

[76] Inventor: Zana S. Goldenberg, 7702 E. Nassau Ave., Denver, Colo. 80237

[21] Appl. No.: 877,904

[22] Filed: May 1, 1992

[51] Int. Cl.$^5$ .............................................. A61F 5/11
[52] U.S. Cl. ...................................... 602/31; 602/30
[58] Field of Search .............................. 602/30, 31

[56] References Cited

U.S. PATENT DOCUMENTS

| | | | |
|---|---|---|---|
| 132,872 | 11/1872 | Stedman | 602/31 |
| 2,342,530 | 2/1944 | Coates | 602/31 |
| 2,499,851 | 3/1950 | Cronholm | 602/31 |
| 2,505,086 | 4/1950 | Andrews | 602/31 |
| 2,920,621 | 1/1960 | Fettig | 602/31 |
| 3,765,410 | 10/1973 | Buens | 602/31 |
| 3,799,160 | 3/1974 | Hahn | 602/31 |
| 3,981,298 | 9/1976 | Vironda | 602/31 |
| 4,674,486 | 6/1987 | Hoffman | 602/31 |
| 4,819,623 | 4/1989 | Ogunro | 602/31 X |

Primary Examiner—Richard J. Apley
Assistant Examiner—Linda C. M. Dvorak
Attorney, Agent, or Firm—Douglass F. Vincent

[57] ABSTRACT

An appliance and method for correcting ingrown toenails. A thin, flat resilient strip is conformed to the shape of the toenail and adhesively attached to the toenail with a suitable adhesive. The strip extends to within one-eighth inch of either opposite side of the toenail, and when so applied, tends to bend resiliently bend back to its original flat shape. The corresponding torque effect created on the toenail is sufficient to cause the affected ingrown toenail to grow out into a naturally correct position. The strip may be of a heat-sensitive material which is more pliable when heat is applied, and which resumes a greater degree of rigidity when the heat is dissipated. Bevelling of the edges around the outer perimeter of the strip smooths the transition of the strip into the surface of the toenail for aesthetic purposes.

2 Claims, 1 Drawing Sheet under 5,261,872

INGROWN TOENAIL CORRECTION APPLIANCE

TECHNICAL FIELD

This invention relates to an appliance for correcting ingrown toenails, and more particularly to an appliance which when applied to an affected toenail will cause the toenail to grow out into a naturally correct position.

BACKGROUND ART

Considerable effort has been expended in solving the problem of correcting ingrown toenails by causing them to grow outwardly into a naturally correct position.

Various apparatus and methods have been utilized to accomplish this result. Generally, the devices used have suffered from the problems of being difficult or even painful to apply, from being uncomfortable to wear when in place on the toenail, from being aesthetically unpleasing, or from having some combination of these problems.

E. E. Stedman in his 1872 U.S. Pat. No. 132,872 discloses an arcuate spring which overlies a toenail engaging the corners thereof and applying an uplifting force. The spring has to be of a length to fit the nail, and is adapted to be hooked under opposite sides of the toenail. Such a device may be painful to apply to the ingrown toenail sufferer, since it requires hooking the ends of the spring under the sides of the toenail, at least one of which sides are ingrown and presumably painful at the time of the treatment. Additionally, the device of Stedman may be difficult to apply, for the same reason that it is painful, i.e., because it must be hooked carefully underneath opposite sides of the toenail, a relatively delicate operation. The device might also be painful to wear, and is also unsightly, not being so designed as to be inconspicuous when worn.

T. L. Marvel in his U.S. Pat. No. 1,213,673 shows a spring member engaging the corners of a toe nail having a reversely curved member extending thereacross exerting a lifting force. This member must also be of a length to fit the nail. The Marvel invention suffers from the same general defects as the Stedman invention, i.e., it is presumably difficult and painful to apply, and also would be uncomfortable and unsightly to wear.

G. W. Smith in his 1923 U.S. Pat. No. 1,451,311 shows an extensible device formed of a pair of flat overlapping resilient members deformed to exert an upward force on the corners of a toenail. The appliance of Smith is subject to the same shortcomings as discussed above with respect to Stedman and Marvel.

H. S. Armagost in his 1946 U.S. Pat. No. 2,405,547 shows a substantially U-shaped wire having looped ends to engage the corners of a toenail, the loops being adapted to and having end portions for digging into the nail for anchorage. The correcting device of Armagost would appear to be more easily applied and possibly less uncomfortable than the above-described inventions. However, being of a narrow wire-type spring construction, the device must necessarily focus pressure in a concentrated area or areas. This is inherently more uncomfortable than a device of a broader-width construction, which would spread the torque and pressure over a wider area of the affected toenail. In addition, the Armagost device remains unsightly, since it causes an arc-shaped bulge on the surface of the toenail.

V. A. Gifford in his U.S. Pat. No. 3,032,032 shows a serpentine wire spring to adjustably extend across a toenail and engage the corners thereof. The Gifford appliance has most of the shortcomings described above with respect to the other inventions in the art.

It would be desirable to provide an appliance for correcting ingrown toenails which would be easily and comfortably applicable to the affected toenail, regardless of the relative skill level of the person applying the device. In addition, the device would preferably be comfortable to wear, since the wearer typically is already in a certain amount of pain from his condition. Finally, a suitable device should be aesthetically pleasing when worn, or at least not aesthetically objectionable. The best that can be expected in this regard is that the device not be noticeable when worn.

DISCLOSURE OF THE INVENTION

In accordance with the present invention, an appliance and a method for correcting ingrown toenails are provided. A thin flat resilient strip is utilized, which is conformed to the shape and size of the toenail and adhesively attached to the toenail with a suitable adhesive. The strip extends to within one-eighth inch of either opposite side of the toenail. When so applied, the strip tends to bend back to its original flat shape, thus creating a corresponding torque effect on the toenail. The torque created in this manner is sufficient to cause most ingrown toenails to grow out into a naturally correct position, yet the torque is light enough to allow the appliance to be virtually painless to wear.

For best results, the strip should cover at least thirty percent of the surface area of the toenail. This relatively broad strip spreads out the torque and the pressure so that the device is comfortable for the user to wear. Optionally, the strip should be of a heat-sensitive material with a shape memory. Heat may thus be applied to the strip as needed prior to attachment to the toenail, thereby making the strip temporarily more pliable and thus facilitating application of the strip to the toenail. After the heat is dissipated, the strip will resume its original degree of rigidity, thus providing added torque to the affected toenail. For aesthetic reasons, the edges of the strip may be bevelled down with a nail file after application, to blend the strip into the toenail so that the appliance is virtually unnoticeable to the average observer.

An appliance and method have thus been provided which will correct an ingrown toenail condition with no discomfort on the part of the user when properly applied. The device is easy and comfortable to apply, comfortable to wear, and virtually unnoticeable by others when properly in place on the toenail.

Additional advantages of this invention will become apparent from the description which follows, taken in conjunction with the accompanying drawings.

BEST MODE FOR CARRYING OUT THE INVENTION

Figure 1:
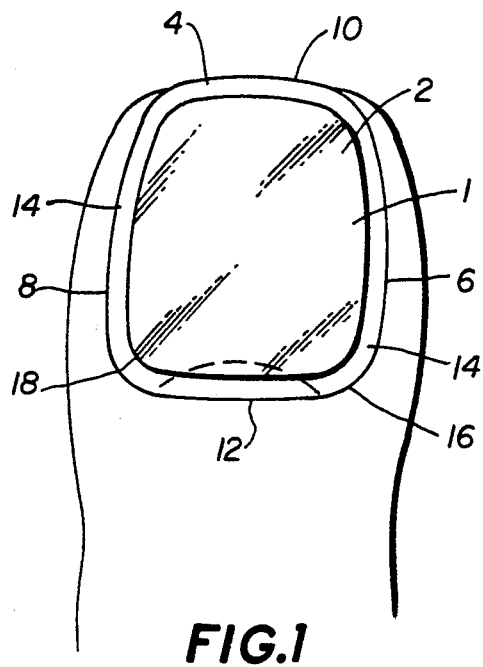
FIG. 1 is a top view of the preferred embodiment of the present invention, depicting an appliance covering the entire area of the toenail except for a border area around the perimeter.
Figure 3:
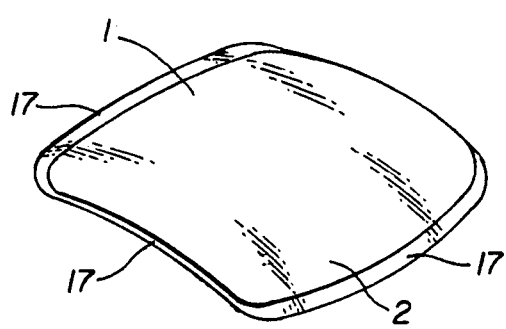
FIG. 3 is a perspective view of the appliance of FIG. 1, showing the general shape and relative thickness thereof.

In accordance with the present invention, as depicted in FIGS. 1 and 3, an appliance for correcting an ingrown toenail is provided which includes a thin, resilient strip 2 for application to the surface of the toenail.

The thin, flat resilient strip 2 is shown in place on a toenail 4 having opposite sides 6,8, and a front edge 10 and a rear edge 12. As shown in this embodiment, the strip 2 extends to within one-eighth inch or less of the sides 6,8 and the edges 10,12, of the toenail 4, forming a border 14 around the perimeter 16 of the toenail. The appliance thus covers a greater surface area of the toe than any previously known device. By covering a larger surface area of the toenail 4, the appliance 1 spreads the pressure to be applied to the toenail over a wider area, which is a significant improvement over a more narrow device such as a wire-type spring which focuses the torque at two particular points on either side of the toenail, as well as placing pressure along a very narrow surface area across the toenail. Additionally, by not hooking into the sides 6,8 of the toenail, the appliance avoids causing the user the pain of having to work directly with the painfully affected flesh area around the ingrown toenail. The fact that the appliance does not hook into the sides of the toenail also provides the advantage of making the appliance much easier to apply than a device which does so hook into the sides of the toenail. Preferably the strip 2 is of a resilient but malleable material such as styrene, which is pliable enough to be easily worked with yet resilient enough to provide the necessary pressure to effect its purpose when in place on the toenail 4. Styrene has the additional advantage of being more pliable when heat is applied, while still having a memory which causes it to resume its original level of rigidity when said heat is dissipated. This is a significant advantage, since a material is desired which is pliable enough to be easily applied yet rigid enough to exert force after application is effected. A certain amount of experimentation is required to discover the optimal material having qualities of pliability when heat-treated, and yet which maintains rigidity in a normal temperature range. Styrene also has the advantage of being a clear material, which enhances the aesthetic quality of the appliance for the wearer by making the appliance far less noticeable.

Referring now to FIG. 3, the strip 2 is first cut to size so that it fits the toenail 4 as depicted in FIG. 1. The strip may then be heat-treated such as by dipping the strip in hot water, so that it becomes pliable and is more easily attached to the toenail. The appliance 1 is then attached to the surface 5 of the toenail 4 using a quick-acting adhesive suitable for such purpose, as for example, cyanoacrylate esther. The adhesive used should be strong enough to provide the necessary bond, should not be affected greatly by changes in temperature and humidity such as might occur in a shower or bath situation, and should be relatively transparent when in use.

Once the appliance 1 has been attached to the toenail 4, the natural resilience of the strip 2 causes it to exert a torque-pressure on the toenail 4 as the strip attempts to resiliently return to its original flat shape. Ideally, this effect will be enhanced by the memory characteristics of the strip which result in a greater rigidity as the strip dissipates the heat which has been applied.

Figure 4:
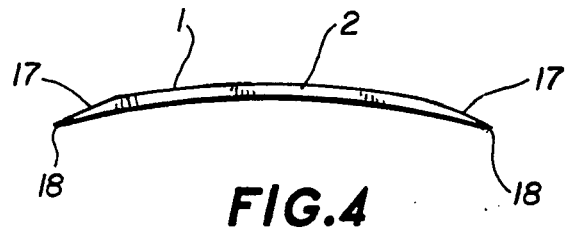
FIG. 4 is a side elevational view of the appliance of FIG. 3, showing the edges around the perimeter of the appliance bevelled down to provide a smooth transition into the surface of the toenail.

Referring now to FIG. 4, the edges 17 around the outer perimeter 18 of the strip 2 have been bevelled down to smooth the transition from the strip 2 into the surface 5 of the toenail 4. In this fashion, the appliance 1 is made to appear to blend into the surface 5 of the toenail 4 as though there were only one continuous surface on the toenail 4. This greatly improves the aesthetic quality of the appliance 1, as the strip 2 may be made virtually unnoticeable when properly applied.

Figure 2:
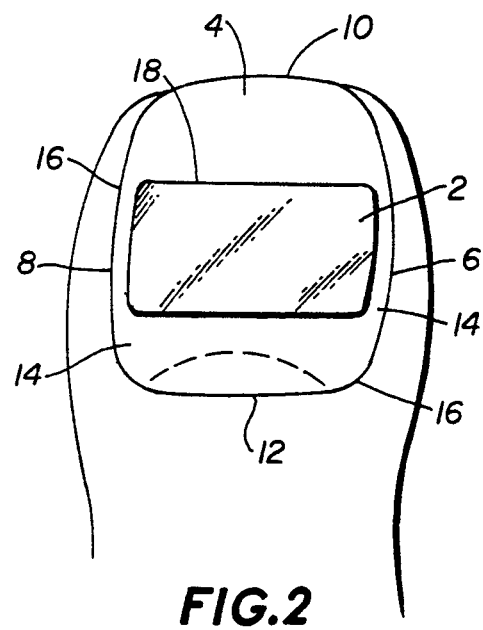
FIG. 2 is a top view of a second embodiment of the present invention, depicting an appliance covering a minimum surface are of the toenail.

As depicted in FIG. 2, the appliance 1 may be of a significantly smaller width, while still being of a sufficient size to accomplish its intended purpose without sacrificing any of its advantages. It has been determined that in order to provide sufficient pressure and still spread that pressure over a large enough area of the toenail 4 to remain relatively painless, the appliance 1 must be large enough to cover at least thirty percent of the surface 5 of the toenail 4.

Based on the above description, several advantages of the present invention are readily apparent. An appliance is provided for causing ingrown toenails to self-correct by gently applying sufficient pressure to cause the toenails to grow outwardly to a naturally correct position. The appliance is easy to apply to the affected toenail, while being comfortable for the wearer during use. In addition, the appliance is virtually unnoticeable when properly applied.

This invention has been described in detail with reference to a particular embodiment thereof, but it will be understood that various other modifications can be effected within the spirit and scope of this invention.

I claim:

1. A method for correcting an ingrown toenail of a user, the toenail having two opposite sides and an upper surface exposed to the air, comprising the steps of:
   providing a thin, flat resilient strip;
   adhesively attaching said strip to the upper surface of the toenail, said strip being cut by the user prior to application so that said strip extends to within a substantially uniform distance of one-eighth inch from either of the opposite sides of the toenail but not extending to the opposite sides of the toenail, said strip when so applied to the toenail being bent to the curvature of the toenail surface of develop an upward torque on the sides of the toenail; and said torque urging said sides upward sufficiently to cause the nail to grow out into a naturally correct position.

2. A method for correcting an ingrown toenail as claimed in claim 1, wherein:
   said strip is heat-sensitive, such that when heat is applied prior to the attachment to the toenail the strip becomes temporarily more pliable, and subsequently resumes a greater degree of rigidity after said applied heat has dissipated;
   said strip is cut to size by the user so that when attached to the toenail surface said strip covers at least thirty percent of the surface area thereof; and
   the outer perimeter of said strip is bevelled so that the strip merges with the toenail in such a way as to give the cosmetic appearance of one continuous surface.

* * * * *